(12) United States Patent
Izatt et al.

(10) Patent No.: US 7,019,838 B2
(45) Date of Patent: Mar. 28, 2006

(54) SYSTEM AND METHOD FOR LOW COHERENCE BROADBAND QUADRATURE INTERFEROMETRY

(75) Inventors: Joseph A. Izatt, Raleigh, NC (US);
Michael Choma, Durham, NC (US);
Changhuei Yang, Pasadena, CA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/855,652

(22) Filed: May 28, 2004

(65) Prior Publication Data

US 2004/0239943 A1    Dec. 2, 2004

Related U.S. Application Data

(60) Provisional application No. 60/474,222, filed on May 30, 2003.

(51) Int. Cl.
*G01B 9/02* (2006.01)

(52) U.S. Cl. ...................... 356/479; 356/497

(58) Field of Classification Search ............... 356/477, 356/479, 497; 250/227.19, 227.27; 385/12
See application file for complete search history.

(56) References Cited

U.S. PATENT DOCUMENTS 5,459,570 A * 10/1995 Swanson et al. ............ 356/479

6,687,008 B1 * 2/2004 Peale et al. ................. 356/477
2004/0239938 A1 * 12/2004 Izatt ........................... 356/450

OTHER PUBLICATIONS

Fiber Optic Sensors, Eric Udd, 1991, pp 284-294.*
Zhao et al: "Real-time phase-resolved functional optical coherence tomography by use of optical Hilbert transformation," Jan. 15, 2002, pp. 98-100, vol. 27, No. 2, Optics Letters, Optical Society of America.

\* cited by examiner

*Primary Examiner*—Hwa (Andrew) Lee
*Assistant Examiner*—Patrick Connolly
(74) *Attorney, Agent, or Firm*—Fleshner & Kim LLP.

(57) ABSTRACT

A quadrature broadband interferometry system and method obtains a complete complex interferometric signal instantaneously in both homodyne and heterodyne systems in a simple, compact, and inexpensive setup. This is accomplished by separating interferometric components from non-interferometric components in each of at least two detector signals of an interferometer having a number of N×N couplers, scaling the interferometric components, and generating real and imaginary parts of a complex interferometric signal from the scaled interferometric components. The detector signals preferably derive from a broadband light source coupled to the interferometer, and the number of N×N couplers may be one or more, with $N \geq 3$.

66 Claims, 8 Drawing Sheets

SYSTEM AND METHOD FOR LOW COHERENCE BROADBAND QUADRATURE INTERFEROMETRY

CROSS-REFERENCE TO RELATED APPLICATIONS

This application claims the benefit of U.S. Provisional Patent Application Ser. No. 60/474,222, filed on May 30, 2003. The contents of this provisional application is incorporated herein by reference.

GOVERNMENT RIGHTS

This invention was made with United States Government support under Federal Grant No. R24 EB000243 awarded by the National Institutes of Health. The United States Government may have certain rights in this invention.

BACKGROUND OF THE INVENTION

1. Field of the Invention

The invention relates to broadband interferometry and, more particularly, to an interferometry system and method in which all components of a complex interferometric signal can be simultaneously acquired.

2. Background of the Related Art

Interferometry with broadband light sources has become a widely used technique for imaging in biologic samples using time-domain optical coherence tomography (OCT), optical coherence microscopy (OCM), spectral domain OCT (which encompasses spectrometer based Fourier domain OCT and swept source OCT), color Doppler OCT, and phase-referenced interferometry. In all of these interferometry techniques, light traveling a reference path is mixed with light returning from or traversing a sample on the surface of a single or multiple detectors.

In homodyne interferometry, the optical frequency of the sample and reference light is the same, and mixing of the fields on the detector results in sum and difference frequency terms corresponding to a second harmonic frequency component and a DC frequency component. The second harmonic frequency component is at twice the optical frequency, and is therefore not resolved by conventional square-law electronic detectors.

In heterodyne interferometry, either the reference or sample arm light is purposefully modulated at a carrier frequency, which results in the difference frequency component residing on a carrier frequency which is electronically detectable. The complete interferometric signal consists of DC components arising from non-mixing light from each of the arms, and interferometric components arising from mixed light. In heterodyne interferometry it is straightforward to separate the DC from interferometric components, since the latter are distinguished by their carrier frequency. In homodyne interferometry, it is impossible to separate the interferometric and non-interferometric components based on their frequency content alone.

In both homodyne and heterodyne interferometers, the interferometric component of the detector signal depends sinusoidally on both the optical path length difference between the arms of the interferometer, and also on an additional phase term which specifies the phase delay between the reference and sample arm fields when the path length difference is zero. When this phase term is zero, the interferometric signal varies as a cosine of the optical path length difference between the arms, and when the phase term is 90 degrees, the interferometric signal varies as a sine of the path length difference. Although a single detector can only detect one of these phase components at a time, it is convenient to refer to the zero and 90 degree phase delayed versions of the interferometric signal as the real and imaginary components (or zero and 90 degree quadrature components) of a complex interferometric signal.

In OCT and many of its variations discussed above, it is often useful or necessary to have access to the entire complex interferometric signal in order to extract amplitude and phase information encoding, scatterer locations and/or motions. For example, in Doppler OCT, multiple phase measurements are required to extract the magnitude and direction of sample motions. In spectral domain OCT, acquiring only one quadrature component of the interferometric signal results in a complex phase ambiguity which does not allow for separation of image information resulting from positive and negative spatial frequencies of the detected data. This ambiguity results in double images, image contamination with undesirable autocorrelation terms, and is wasteful of detector pixels (in Fourier domain OCT) and data collection time (in swept source OCT). Unfortunately, the square-law detector output which is available in previously disclosed OCT systems and their variations obtains only the real part of the complex signal (in the case of single receiver systems), or the real part and its inverse (in the case of differential receiver systems).

Several methods have been reported which allow for instantaneous or sequential retrieval of both quadrature components of the complex interferometric signal. These include 1) polarization quadrature encoding, where orthogonal polarization states encode the real and imaginary components; 2) phase stepping, where the reference reflector is serially displaced, thus time encoding the real and imaginary components; and 3) synchronous detection, where the photodetector output is mixed with an electronic local oscillator at the heterodyne frequency. Synchronous detection methods include lock-in detection and phase-locked loops. Polarization quadrature encoding and phase stepping can be generically called quadrature interferometry since the complex signal is optically generated. As such, they are useful in both homodyne and heterodyne systems.

Each of these techniques suffers from shortcomings. Polarization quadrature encoding is instantaneous, but it requires a complicated setup, and suffers from polarization fading. Phase shifting requires a stable and carefully calibrated reference arm step, is not instantaneous, and is sensitive to interferometer drift between phase-shifted acquisitions. Synchronous detection is not instantaneous, and depends on the presence of an electronic carrier frequency. Systems based on synchronous detection are thus not useful in an important class of homodyne systems, such as en-face imaging schemes, those which take advantage of array detection (e.g. Fourier domain OCT), and in swept source OCT.

There is thus a clear need for a system and method for instantaneous and simultaneous acquisition of both quadrature components of the complex interferometric signal in OCT and related systems.

SUMMARY OF THE INVENTION

An object of the invention is to solve at least the above problems and/or disadvantages and to provide at least the advantages described hereinafter.

Another object of the invention is to provide a quadrature broadband interferometry system and method that can obtain the complete complex interferometric signal instantaneously in both homodyne and heterodyne systems in a simple, compact, and inexpensive setup.

To achieve these and other objects and advantages, the present invention provides an improved system and method for quadrature broadband interferometry which exploit the inherent phase shifts of N×N (N>2) fiber optic couplers to obtain the complete complex interferometric signal instantaneously in both homodyne and heterodyne systems.

In accordance with one embodiment, the present invention provides a signal processing method which includes separating interferometric components from non-interferometric components in each of at least two detector signals of an interferometer having a number of N×N couplers, scaling the interferometric components, and generating real and imaginary parts of a complex interferometric signal from the scaled interferometric components. The detector signals preferably derive from a broadband light source coupled to the interferometer. Also, the number of N×N couplers may be one or more, with $N \geq 3$.

Separating the interferometric components may be performed by high-pass or band-pass filtering signals output from the detectors. This separation may also be accomplished by extracting AC-coupled signals from signals output from the detectors. Such an extraction may be performed by removing at least one of DC components, source noise components, and auto-correlation terms from the detector outputs prior to re-scaling.

Scaling the interferometric components may be performed by phase shifting the interferometric components of the two detector signals to have a predetermined phase difference. The interferometric components are preferably shifted to have orthogonal phases, although other phase relationships are possible. Scaling may also be performed to reduce optical losses which correspond, for example, to at least one of optical path losses and variations in gain between different ones of the detectors.

Generating the imaginary part of the complex interferometric signal from the real part may be performed based on a method derived from the cosine sum rule. Once the real and imaginary parts are obtained, a Doppler shift value may be calculated based on a time derivative of the calculated phase.

In accordance with another embodiment, the present invention provides an analyzer which includes an interferometer including at least one fiber-optic coupler, a number of detectors that detect light from said at least one coupler, and a processor which acquires interferometric components from signals output from the detectors, scales the interferometric components, and generates real and imaginary parts of a complex interferometric signal from the scaled interferometric components.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Fused-fiber couplers rely on evanescent wave coupling to split an input electric field between output fiber paths, according to coupled-mode theory. (It is to be understood that an optical signal is one type of electric field that may be subject to the present invention. In a broader sense, the embodiment of the present invention disclosed herein may be applied to any type of electromagnetic radiation). A formalism based on conservation of energy which predicts phase shifts for interferometers based on 2×2 and 3×3 couplers will now be described. While higher-order couplers (e.g. 4×4) can be used in a manner similar to that described below for 3×3 couplers to acquire the complex interferometric signal, the phase shifts in these couplers only can be explained by coupled-mode theory.

Figure 1A:
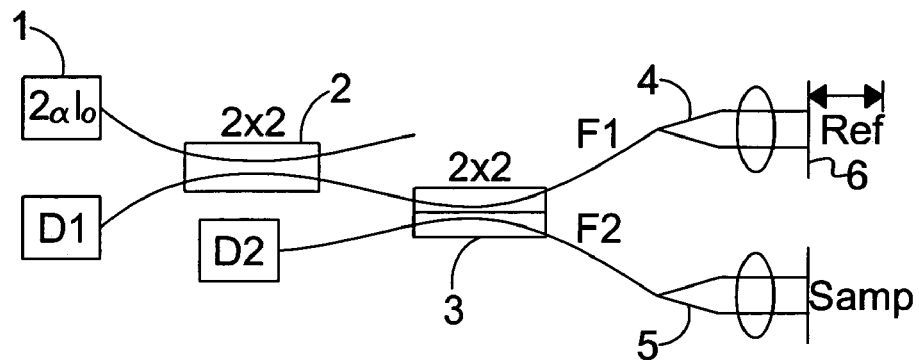
FIG. 1A is a schematic diagram of a differential low-coherence Michelson interferometer based on 2×2 fiber couplers in accordance with one embodiment of the present invention.
Figure 1B:
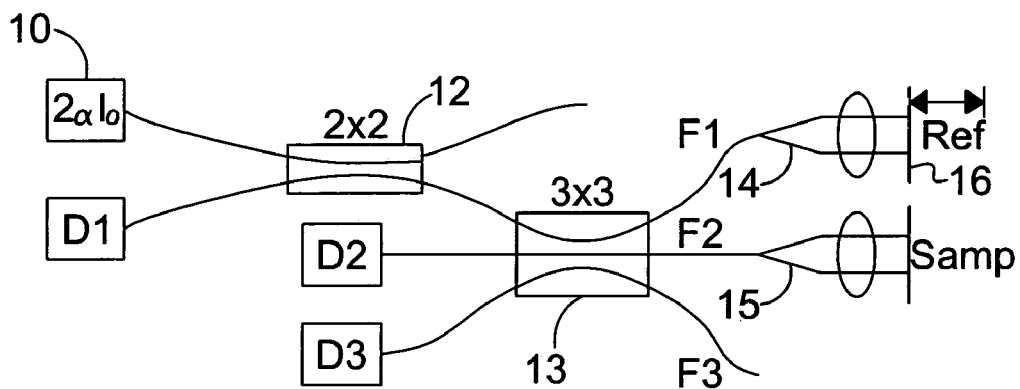
FIG. 1B is a schematic diagram of a Michelson interferometer based on a 3×3 fiber coupler in accordance with one embodiment of the present invention.

FIGS. 1A and 1B respectively show examples of 2×2 and 3×3 coupler-based Michelson interferometers in accordance with the present invention. In these and subsequent figures, coupling coefficients may be denoted by $\alpha_{ab}$, which describes the power transfer from one fiber or optical path a to another fiber or optical path b. For example, the 2×2 coupler may have a 50/50 split ratio where $\alpha_{11}=\alpha_{12}=\frac{1}{2}$, and the 3×3 coupler may have a 33/33/33 ratio where $\alpha_{11}=\alpha_{12}=\alpha_{13}=\frac{1}{3}$. Alternative embodiments of the invention may use couplers with disproportionate split ratios if desired.

The FIG. 1A interferometer includes a source 1, two fiber-optic couplers 2 and 3, and reference and sample arms 4 and 5. The light source is preferably a broadband light source (e.g., one having multiple wavelengths or modes), however a narrowband source may be used if desired. The source is shown as $2\gamma I_0$ for reasons that will become more apparent below. In this embodiment, the couplers are both 2×2 couplers. The first coupler splits light from the source along two optical paths, one of which is input into the second coupler. The second coupler splits this beam along fibers F1 and F2 which respectively lead to the reference and sample arms. At least the reference arm terminates with a reflector 6. The sample serves as the reflection source of the other arm.

Light beams reflected from the reference and sample arms are re-combined in coupler 3. A portion of this re-combined light is then detected by detector D2, and another portion of this light is input into coupler 2, where it is detected by detector D1. As will be described in greater detail below, the detector signals may be processed to derive a complex interferometric signal in accordance with the present invention.

The FIG. 1B interferometer includes a source 10, two fiber-optic couplers 12 and 13, and reference and sample arms 14 and 15. The light source is preferably a broadband light source (e.g., one having multiple wavelengths or modes), however a narrowband source may be used if desired. The source is shown as $2\gamma I_0$ for reasons that will become more apparent below. In this embodiment, the first coupler is a 2×2 coupler and the second coupler is an N×N coupler, where $N \geq 3$. For illustrative purposes, N=3 in the figure.

The first coupler splits light from the source along two optical paths, one of which is input into the second coupler. The second coupler splits this beam along fibers F1 and F2 which respectively lead to the reference and sample arms. Light beams reflected from these arms are re-combined in coupler 13. Portions of this re-combined light is then detected by detectors D2 and D3, and another portion of the re-combined light is input into coupler 12, where it is detected by detector D1. As in the previous embodiment, the reference arm may terminate with a reflector 16 and the sample may reflect the light in the sample arm.

The detector signals may differ in respect to their phase, e.g., the phase of the interference signal on detectors D2 and D3 may be different. For example, if the 3×3 coupler has a splitting ratio of 1/3:1/3:1/3, then the interference signals on D2 and D3 will be out of phase by 120 degrees. The amplitude of the interference signals may also be different, if the splitting ratio is something other than 1/3:1/3:1/3. The amplitudes will also be different if detectors D2 and D3 have different electronic gains.

In FIGS. 1A and 1B, the first coupler may be used to allow for detection of that portion of the interferometric signal which would otherwise return to the source. In other embodiments of the invention, the first coupler may be replaced by an optical circulator (if all returning components of the interferometric signal are required) or eliminated entirely (if all but one of the returning components are sufficient for signal processing). Ignoring the return loss from the source arm 50/50 coupler, the optical intensity incident on the $n^{th}$ detector due to a single reflection in the sample is:

$$I_n = \gamma I_0(\alpha_{11}\alpha_{1n} + \alpha_{12}\alpha_{2n} + 2E(\Delta x) \sqrt{\alpha_{11}\alpha_{1n}\alpha_{12}\alpha_{2n}} \cos(2k\Delta x + \phi_n)), \quad (1)$$

where k is the optical wavenumber, $\Delta x$ is the path length difference between reflectors in the reference and sample arms, $E(\Delta x)$ is the interferometric envelope (i.e. the magnitude of the complex signal), and $\phi_n$ is the phase shift between the detector photocurrents. This phase shift is imparted by the evanescent wave coupling process. Also, $\gamma$ ensures that the total power incident on the reference and sample arms is $I_0$, e.g. $\gamma$ is 1 for a 2×2 and $\gamma=1/(\alpha_{11}+\alpha_{12})$ for a 3×3.

Since the non-interferometric portions of $I_n$ sum to $I_0$, the interferometric portions must sum to zero, independent of $\Delta x$. Assuming perfect reciprocity (i.e. $\alpha_{ab}=\alpha_{ba}$), losslessness $$\left(\sum_n \alpha_{an} = 1\right),$$

and directionality (no internal coupling from input back into input fibers) in the fiber coupler, this implies that:

$$\text{Re}\left\{\sum_n \sqrt{\alpha_{1n}\alpha_{2n}} \exp(j2k\Delta x)\exp(j\phi_n)\right\} = 0; \quad (2a)$$

$$\sum_n \sqrt{\alpha_{1n}\alpha_{2n}} \cos(\phi_n) = \sum_n \sqrt{\alpha_{1n}\alpha_{2n}} \sin(\phi_n) = 0. \quad (2b)$$

Because variations in $k\Delta x$ rotate the $(\alpha_{1n}\alpha_{2n})^{1/2}\exp(j\phi_n)$ vector in the complex plane (Eq. 2a), Eq. 2a is true if and only if $(\alpha_{1n}\alpha_{2n})^{1/2}\exp(j\phi_n)$ sum to zero (Eq. 2b). These equations demand that $|\phi_1-\phi_2|=180°$ for 2×2 couplers, regardless of the coupler splitting ratio, while $\phi_m-\phi_n$ is an explicit function of $\alpha_{ab}$ for 3×3 couplers.

Figure 1C:
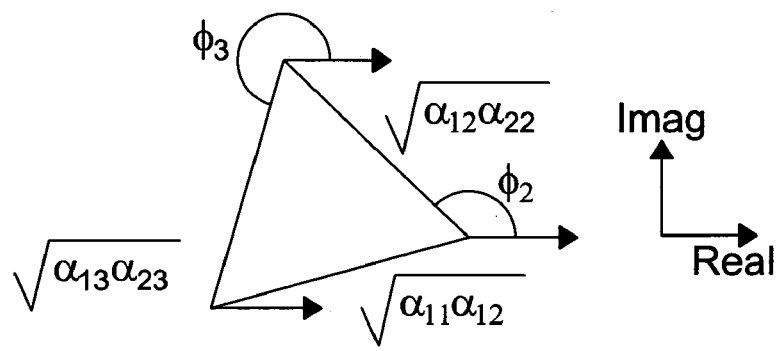
FIG. 1C is a graphical representation of the intrinsic phase shifts in a 3×3 coupler-based Michelson interferometer in accordance with one embodiment of the present invention.

FIG. 1C shows one way in which Eq. 2b may be graphically represented as a sum of three complex vectors with magnitude $(\alpha_{1n}\alpha_{2n})^{1/2}$ and phase $\phi_n$. Given a set of measured values of $\alpha_{ab}$, the interferometric phase shifts between coupler arms $\phi_m-\phi_n$ are uniquely determined, since the three vectors correspond to the sides of a triangle whose inner angles are related to $\phi_m-\phi_n$. For example, if $\alpha_{ab}=\frac{1}{3}$ for all fibers a and b, then the interferometric phase shift between any two output ports of a 3×3 Michelson interferometer is 120°.

For 4×4 and higher order couplers, Eqs. (1)–(2b) are still valid, but are not sufficient to uniquely predict the interferometric phase shifts between coupler arms $\phi_m-\phi_n$ as a function of the coupling ratios. However, 4×4 and higher order couplers may be extremely useful for instantaneous quadrature interferometry, especially by specifically designing them to give phase angles separated by 90°, in that they give all in-phase, quadrature, and out-of-phase components (0°, 90°, 180°, 270°) of the complex interferometric signal without requiring any further signal processing.

Extracting Complex Interferometric Data from N×N Interferometers

Because the phase shifts among $I_n$ in Eq. (1) are not constrained to be 0° or 180° for interferometers based on 3×3 and higher-order couplers, the complex interferometric signal can be obtained instantaneously from simultaneous measurements of any two or more detector outputs. It should be appreciated that this can be accomplished with all higher-order N×N interferometers (N>2) of various topologies (e.g. Michelson, Mach-Zehnder, etc.). The detectors are preferably connected to a processor (not shown) which performs computations for deriving the complex interferometric signal.

A method for extracting the real and imaginary components of the complex interferometric signal from the interferometer detector outputs, corresponding to detectors located on all N×N input fibers, and on any unused output detectors, will now be described with reference to FIG. 2.

Figure 2:
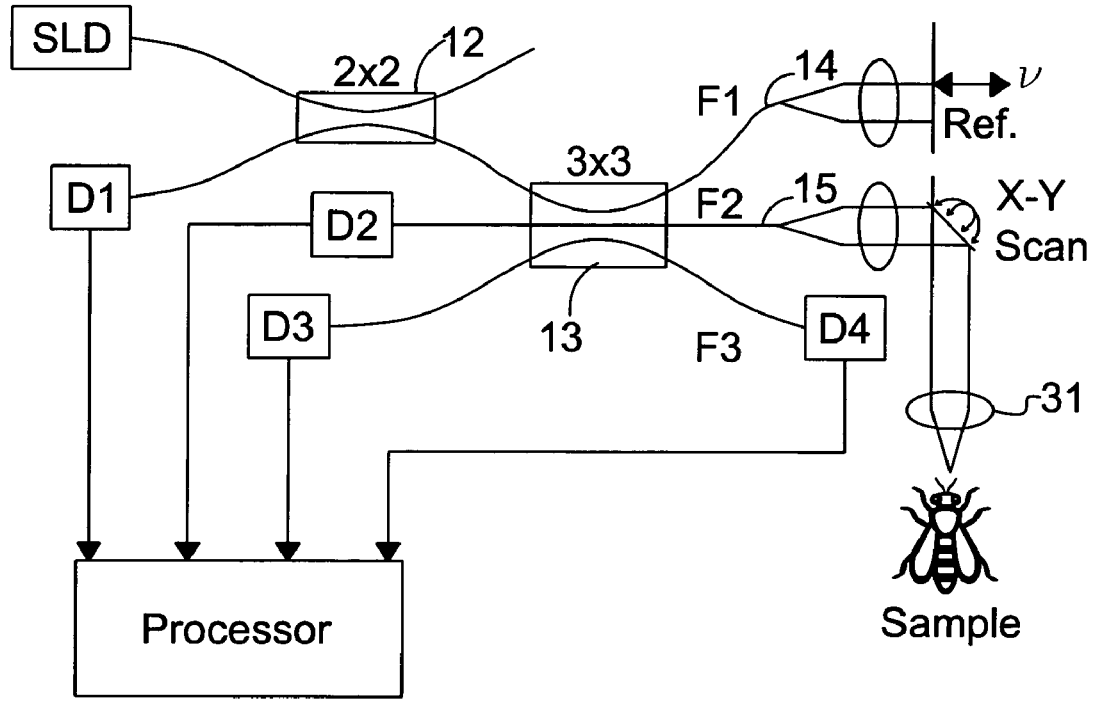
FIG. 2 is a schematic diagram of a 3×3 coupler-based interferometer with all potential detector locations populated in accordance with one embodiment of the present invention.

FIG. 2 shows a 3×3 interferometer in accordance with another embodiment of the present invention. This interferometer may be constructed in a manner similar to FIG. 1B, except that a detector D4 is attached to optical fiber F3, an X-Y scanning mirror 30 is used to scan and capture reflected light from a sample (which in this case is illustratively shown as insect), and a superluminescent diode (SLD) serves as the broadband light source. An optional lens 31 may be included to focus the light into and out of the scanning mirror. The FIG. 2 embodiment also includes a processor 35 which processes signals from at least two detectors to compute a complex interferometric signal in accordance with the present invention. (While only FIG. 2 shows this processor, it is understood that other embodiments described herein also include a processor for generating a complex interferometric signal from detector signals or pairs of detector signals).

The first step in extraction of the complex interferometric data from N×N interferometers is to separate out the interferometric components of at least two detector signals from the non-interferometric or DC components. DC components, as used herein, refer both to any non-interferometric light appearing on detector outputs due to amplitude or polarization mismatch between sample and reference arms, as well as to any autocorrelation terms resulting from multiple partial reflections occurring in either sample or reference arms.

Removing DC components is critical to obtaining the complex interferometric signal, and is also useful in optimizing signal-to-noise ratio in OCT systems, since these DC components also contain light source fluctuations (excess noise) which are common mode to light returning from the sample and reference arms. Cancellation of common-mode source noise and removal of autocorrelation terms may be accomplished by some of the techniques that will now be described.

In heterodyne systems, selection of interferometric components is done by AC coupling or high-pass filtering all input fiber detector outputs (e.g., detectors $D_1$ through $D_3$ in FIG. 2) with a cutoff frequency below the heterodyne carrier frequency. An alternatively approach would involve bandpass filtering around the heterodyne carrier frequency. In homodyne systems, where AC coupling is not an option, AC coupling may be simulated by separately measuring the DC level appearing on each input fiber detector output (detectors $D_1$ through $D_3$ in FIG. 2) due to the reference arm DC level and sample arm DC level measured separately, then subsequently subtracting these DC levels from each respective detector output during interferometric measurements. In the usual case in OCT, where the quantity of light reflected from the sample is small compared to the reference arm recoupling, this procedure may be approximated by subtracting only the reference arm recoupled DC level from each of the detector outputs.

Simulating AC coupling by pre-measuring DC recoupling into each of the input fiber detectors is sufficient for reconstruction of the complex interferometric signal, but does not remove the common-mode source noise or autocorrelation terms. Two techniques will now be described which accomplish all three tasks simultaneously.

If detector outputs are available from all input fibers of the N×N interferometer (detectors $D_1$ through $D_3$ in FIG. 2), then the DC level to be subtracted from each detector, including source fluctuations and autocorrelation terms, may be obtained by summing all detector outputs, scaled by any loss experienced on the path back to each detector. For the embodiment of FIG. 2, the ideal total re-coupled power is given by $D_T=2*D_1+D_2+D_3$, where the factor of 2 multiplying $D_1$ arises from the insertion loss of the 2×2 coupler in the source arm. Given this measurement of $D_T$, each detector output may be effectively AC coupled by subtraction of the proper fraction of $D_T$ from that output, i.e. $D_1^{AC}=D_1-D_T/6$, $D_2^{AC}=D_2-D_T/3$, and $D_3^{AC}=D_3-D_T/3$. These equations should be corrected in view of the exact coupling ratios and any additional losses present upstream of each detector in any system implementation.

A second technique for removal of DC components, including source fluctuations (but not autocorrelation terms), from the detector outputs involves the use of any unused output fiber of the N×N interferometer (e.g., detector $D_4$ in FIG. 2). In the embodiment of FIG. 2, the AC-coupled input fiber detector outputs are given approximately by $D_1^{AC}=D_1-\gamma_1*D_1/2$, $D_2^{AC}=D_2-\gamma_2*D_2$, and $D_3^{AC}=D_3-\gamma_3*D_3$. Here, the quantities $\gamma_n$ are proportionality constants, which depend upon the specific recoupling ratios of light from sample and reference arms back into the N×N coupler, as well as specific losses in each detector arm, and would likely have to be separately characterized for each instrument.

Following the removal of DC components, source noise fluctuations, and autocorrelation terms from each of the detector outputs in an N×N coupler-based interferometer system, each detector output is preferably re-scaled to compensate for specific losses in the optical path to each detector, as well as for variations in the gain between different detectors, before proceeding to complex interferogram extraction. For example, in the interferometer of FIG. 2, the output of detector $D_1$ must be multiplied by a factor of 2 to compensate for the presence of the 2×2 coupler between detector $D_1$ and the 3×3 coupler. The exact values for re-scaling of each detector output will depend on the specific pattern and/or characteristics of the optical losses and electronic gains associated with each detector's optical and electronic paths.

The complex interferometric signal may be extracted from the AC-coupled and re-scaled detector outputs. A technique for reconstructing the complex interferometric signal uses the AC-coupled and re-scaled signal from any two detectors located on input fibers of the N×N coupler (e.g. detectors $D_1-D_3$ in FIG. 2). Defining $i_n$ as the interferometric portion of $I_n$, and assigning any $i_n$ as the real part of the complex signal (denoted $i_{Re}$ below), then the imaginary part $i_{Im}=2E(\Delta x)(\alpha_{11}\alpha_{1n}\alpha_{12}\alpha_{2n})^{1/2}\sin(2k\Delta x+\phi_n)$, may be obtained by using the cosine sum rule, as:

$$i_{lm} = \frac{i_n \cos(\phi_m - \phi_n) - \beta i_m}{\sin(\phi_m - \phi_n)}, \beta = \sqrt{\frac{\alpha_{11}\alpha_{1n}\alpha_{12}\alpha_{2n}}{\alpha_{11}\alpha_{1m}\alpha_{12}\alpha_{2m}}}. \quad (3)$$

The re-scaling of the $m^{th}$ detector output is expressed as an explicit function of the coupling coefficients of the N×N coupler. The re-scaling parameter $\beta$ may also be obtained experimentally, as described above. Once $i_{Re}$ and $i_{Im}$ are obtained according to Eq. (3), then the magnitude and phase of the complex interferometric signal may be obtained according to standard formulas from complex mathematics.

The technique summarized by Eq. (3) may be applied to any 2 detector outputs (located on an input fiber to the N×N coupler) of an N×N interferometer. If multiple pairs of outputs are available (e.g., detectors $D_1$&$D_2$, $D_2$&$D_3$, $D_1$&$D_3$ in FIG. 2), then an improved estimate of the interferometric amplitude and phase may be applied by averaging the amplitudes and phases obtained from the application of the technique of Eq. (3) to each detector pair calculated separately.

Figure 3:
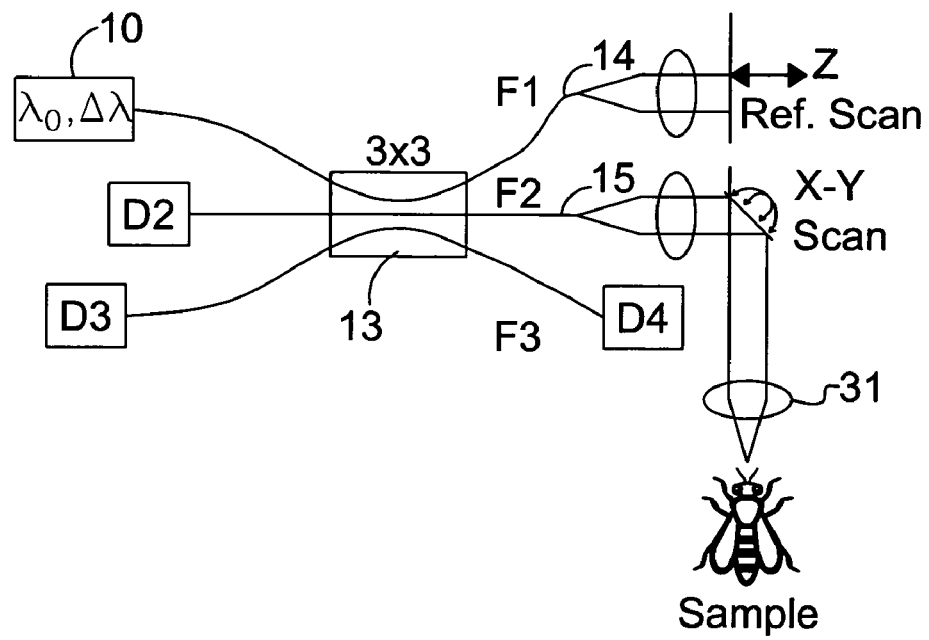
FIG. 3 is a schematic diagram of a 3×3 coupler-based interferometer that provides simultaneous detector outputs with 120 degree phase separation and a DC component that includes source fluctuations in accordance with one embodiment of the present invention.

FIG. 3 shows another particularly robust instantaneous quadrature interferometer system in accordance with the present invention. This system takes advantage of the technique described by Eq. (2) and includes a 3×3 coupler-based interferometer without a 2×2 coupler. In this embodiment, the broadband source is shown as $\lambda_0$, $\Delta\lambda$, where $\lambda_0$ corresponds to the source center wavelength and $\Delta\lambda$ corresponds to the bandwidth. Also, the optical signal reflected in the reference arm is generated by a Z-reference scan. Through this arrangement, the quadrature output is simplified from Eq. (3) as $I_{90} \propto (I_{120} - I_0 \cos(120°))$, and A scans can then be processed based on this derived output and the original 0° detector output.

In the case of a 4×4 coupler, quadrature and differential spectra are available directly from the three unused input ports, although the overall power utilization efficiency is slightly less than in the 3×3 coupler case. In both 3×3 and 4×4 coupler cases, all required signals are available from the unused input ports. Thus, a circulator or input 2×2 coupler is not required, as is included in the embodiments of FIGS. 1A and 1B. The implementation of the system of FIG. 3 could be extremely robust, as no optics or mechanics are required in the reference arm path at all. For example, the reference arm path could simply be a length of fiber with a reflective end coating coiled in a box. Of course, any mismatch in fiber lengths between the sample and reference arms will need to be dispersion compensated using known techniques.

Instantaneous Quadrature Interferometry with N×N Interferometers

Figure 4:
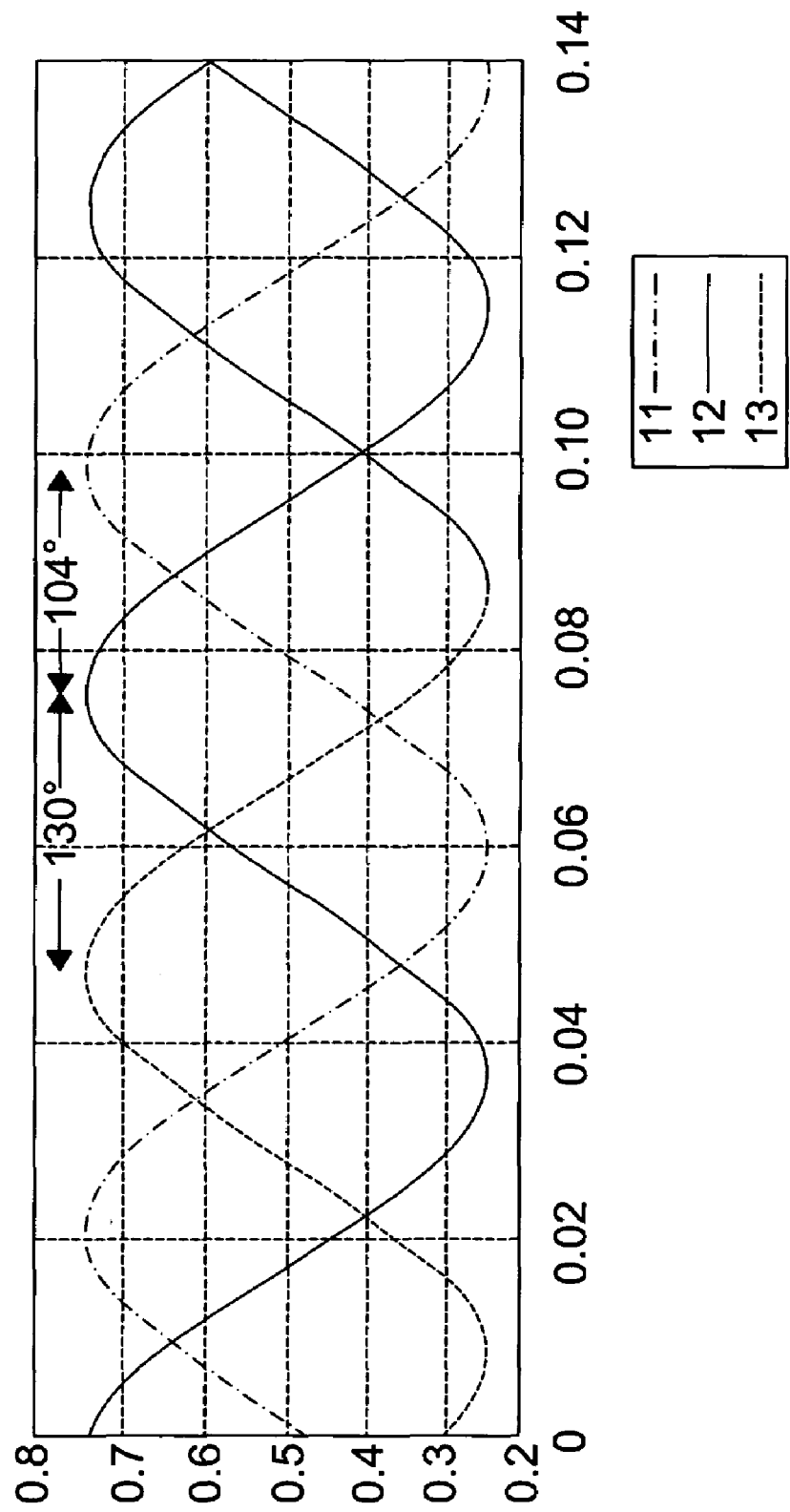
FIG. 4 is a plot of the interferometric detector outputs of the 3×3 coupler-based Michelson interferometer embodiment of FIG. 1B during a heterodyne experiment, in which amplitudes have been normalized, in accordance with one embodiment of the present invention.

The embodiment of FIG. 1B has been tested using a superluminescent diode source (OptoSpeed; $\lambda_o$=1274 nm, $\Delta\lambda$=28 nm) and an AC Photonics, Inc. 3×3 truly fused fiber coupler. To demonstrate instantaneous quadrature signal acquisition in a heterodyne experiment, the reference arm was scanned at $v$=8.3 mm/sec. The interferometric portion of all three acquired photodetector outputs is illustrated in FIG. 4. The phase shifts between detector outputs were measured to be $\phi_3 - \phi_2 = 130.8°$ and $\phi_1 - \phi_2 = 255.4$.

When experimentally measured values of $\alpha_{ab}$ were used to solve for the theoretical interferometric phase shifts (Eqs. 2a and 2b), these theoretical shifts deviated from the experimental shifts by $\leq 2.5\%$ (FIG. 1C). $\phi_m - \phi_n$ drifted over the course of minutes to hours, and it is believed that these drifts are due to temperature sensitivity of the coupler splitting ratio.

Figure 5A:
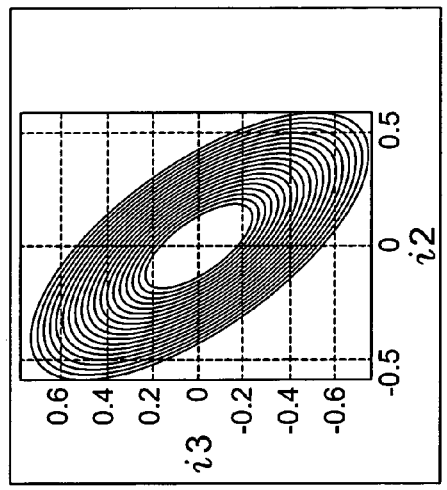
FIG. 5A is a three-dimensional Lissajous plot of the interferometric signal from three photodetectors in the 3×3 coupler-based Michelson interferometer of FIG. 1B.

If $i_1$, $i_2$, and $i_3$ are parametrically plotted against each other, a three-dimensional Lissajous curve may be formed, as shown in the plot of FIG. 5A. Time is encoded by the color of the curve: in this experiment the data was captured as $\Delta x$ increased with time, and the curve spirals outwards from the center and transitions from green to black to red. (The green color corresponds to an inner portion including an inner circumferential portion of the curve, the black color corresponds to an intermediate portion of the curve, and the red color corresponds to an outer portion including an outer circumferential portion of the curve). The curve fills an ellipse.

Figure 5B:
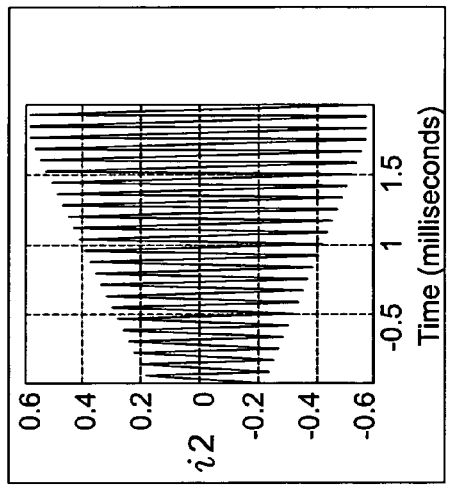
FIG. 5B is a Lissajous plot of interferometric signal $i_3$ vs. interferometric signal $i_2$ for the 3×3 coupler-based Michelson interferometer of FIG. 1B.
Figure 5C:
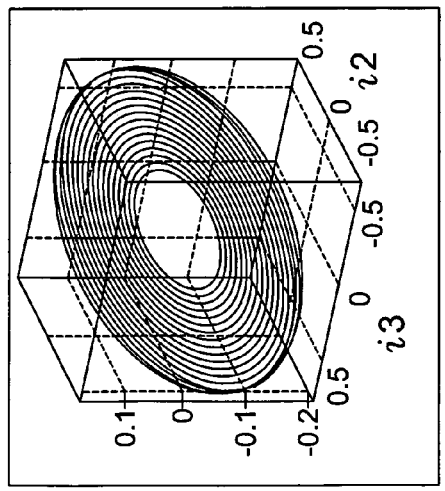
FIG. 5C is a plot of real vs. imaginary signals calculated from interferometric signals $i_2$ and $i_3$ for the 3×3 coupler-based Michelson interferometer of FIG. 1B.
Figure 5D:
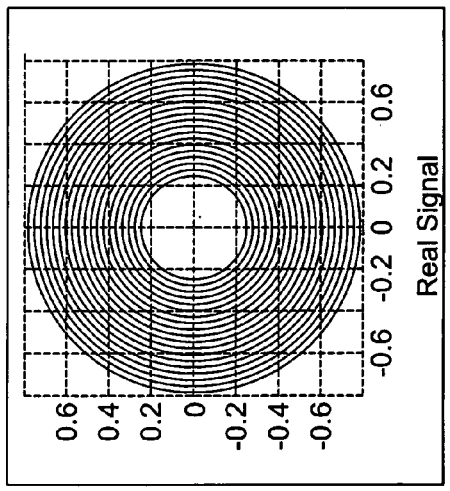
FIG. 5D is a plot of interferometric signal vs. time for the 3×3 coupler-based Michelson interferometer of FIG. 1B.
Figure 6:
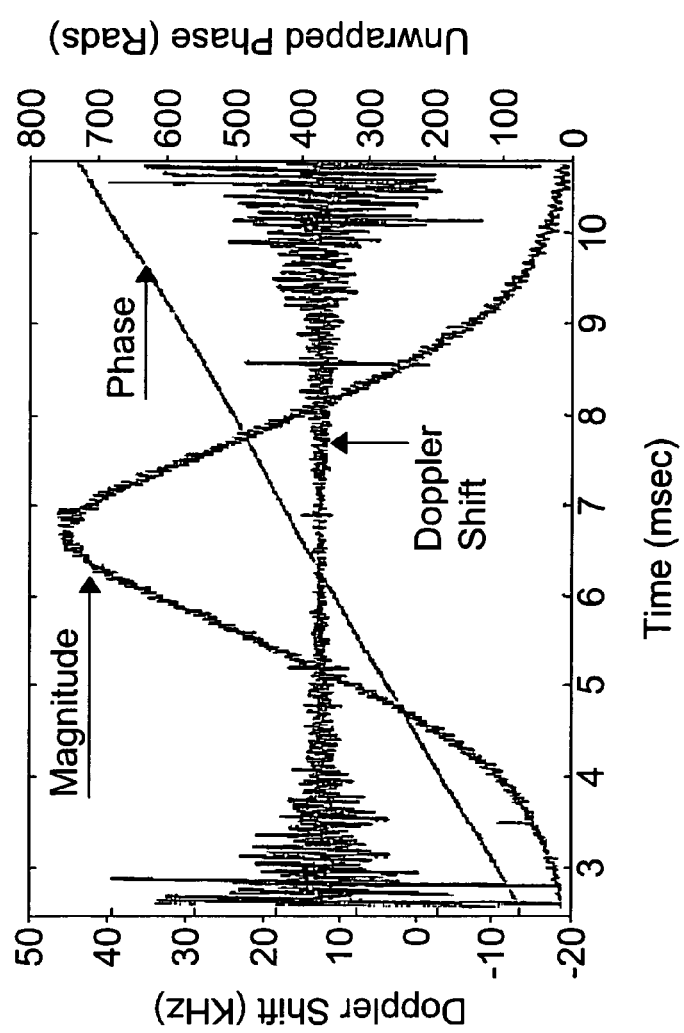
FIG. 6 is a plot of the magnitude, phase and Doppler shift of the complex heterodyne interferometric signal calculated from outputs of the 3×3 coupled-based Michelson interferometer of FIG. 1B.
Figure 7:
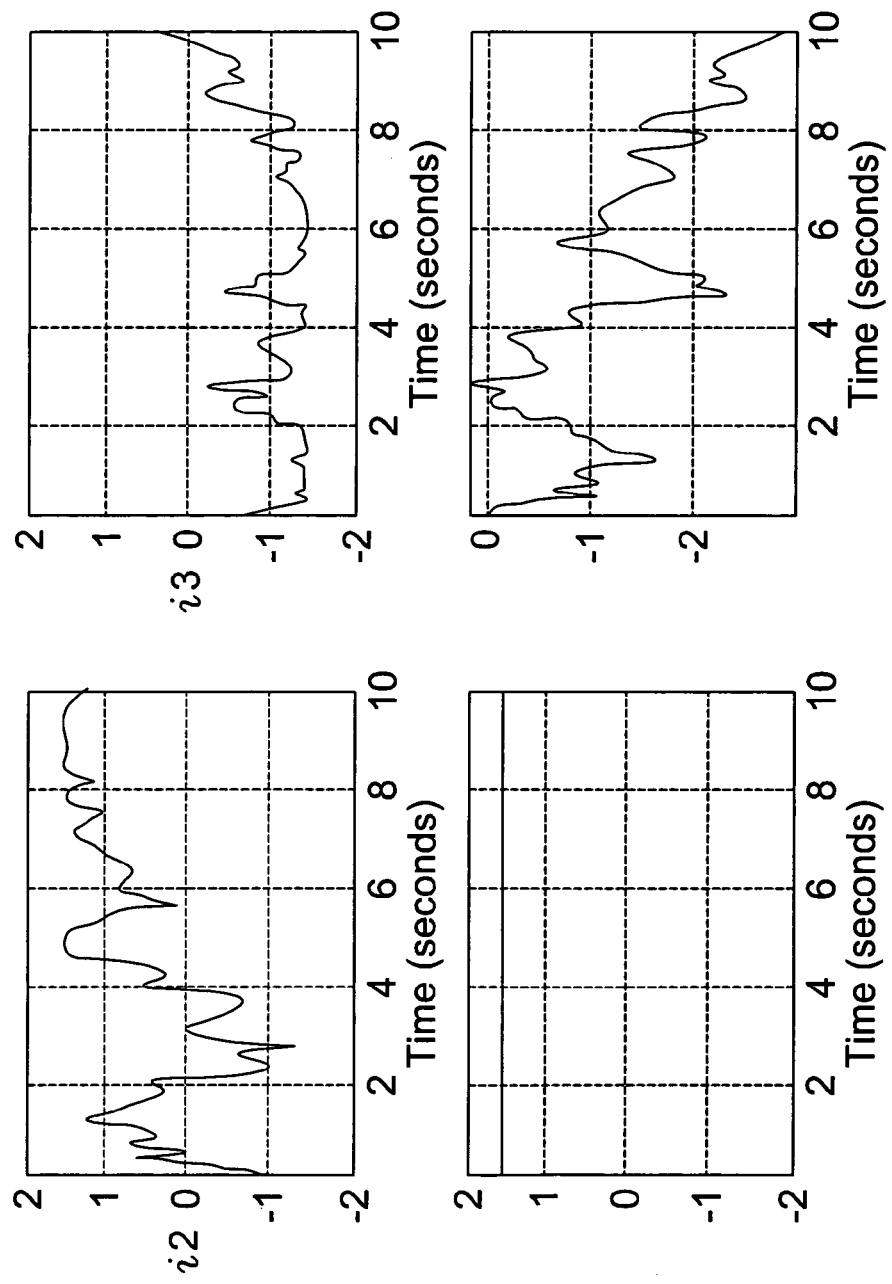
FIGS. 7A–7D are graphs showing plots of the magnitudes and phases of the complex interferometric signal for a homodyne experiment using the embodiment of FIG. 1B.

FIG. 5B is a Lissajous plot of interferometric signal $i_3$ vs. interferometric signal $i_2$, where the progression of color from green to black to red is similar to the pattern in FIG. 5A. FIG. 5D is a plot of interferometric signal vs. time. In this plot color progresses from green to black to red with increasing time. The real ($i_2$) and imaginary parts (calculated from Eq. 3) of the interferogram are plotted as a Lissajous curve in FIG. 5C with the same color pattern as in FIGS. 5A and B. The real and imaginary parts were used to calculate the magnitude and phase as plotted in FIG. 6. The time derivative of the phase yields the Doppler shift $f_d$ generated by the scanning reference mirror:

$$\frac{d\text{phase}}{dt} = f_d = \frac{2v}{\lambda} \quad (4)$$

The experimentally-calculated Doppler shift (FIG. 6) agrees well with the predicted value of 13 kHz, based on the calibrated scan velocity of the reference arm. This result demonstrates the utility of N×N interferometers in color Doppler OCT.

A 3×3 instantaneous quadrature signal acquisition in a homodyne experiment has also been demonstrated by positioning a non-scanning reference mirror (v=0) such that $\Delta x$ corresponds to the middle of an interferogram. The outputs $i_2$ and $i_3$ (from detectors D2 and D3) were then recorded for 10 seconds, and Eq. (3) was used to reconstruct amplitude and phase. Due to interferometer drift on the order of $\sim\lambda$, the phase of the complex interferometric signal varied by $\sim 2\pi$, while the magnitude remained steady (mean=1.52, variance=$1.96 \times 10^{-4}$. This is shown in FIGS. 7A–7D, which are plots of the magnitude and phase of the complex interferometric signal for the homodyne experiment using the embodiment of FIG. 1B. This result demonstrates the utility of N×N interferometers in homodyne OCT setups such as optical coherence microscopy, Fourier-domain OCT, and swept source OCT.

Although higher-order N×N (N>2) interferometers are less efficient with source light than 2×2 interferometers, they are more efficient at collecting light reflected from the sample, and may thus be advantageous in exposure-limited applications, such as retinal imaging. For example, the 3×3 coupler-based interferometer of FIG. 1B delivers only ⅙ of the source light to the sample, but collects ⅓+⅓+(⅓)(½) =83% of the light returning from the sample. Replacing the first 2×2 coupler in FIG. 1B with a circulator would result in sample reflected light collection efficiency limited only by the insertion loss of the circulator.

The simpler embodiment of FIG. 3 delivers ⅓ of the source light to the sample, and collects ⅔ of the light returning from the sample. By modeling and analysis, it is possible to optimize source utilization efficiency, sample return utilization efficiency, or some combination by proper specification of N×N coupler splitting ratios.

As described above, N×N interferometers allow for instantaneous optical extraction of magnitude and phase information simultaneously in a compact and simple design. Their advantages are particularly compelling in FD-OCT and swept source OCT, where they allow for optical resolution of the complex conjugate ambiguity without phase stepping.

Higher Order Interferometric Topologies

The analysis described above, including the governing equations for N×N interferometers (Eqs. 1–3) and the disclosed techniques for recovering the complex interferometric signal from the raw detector outputs, are generalizable to N×N interferometers based on arbitrarily high order N×N couplers.

Figure 8:
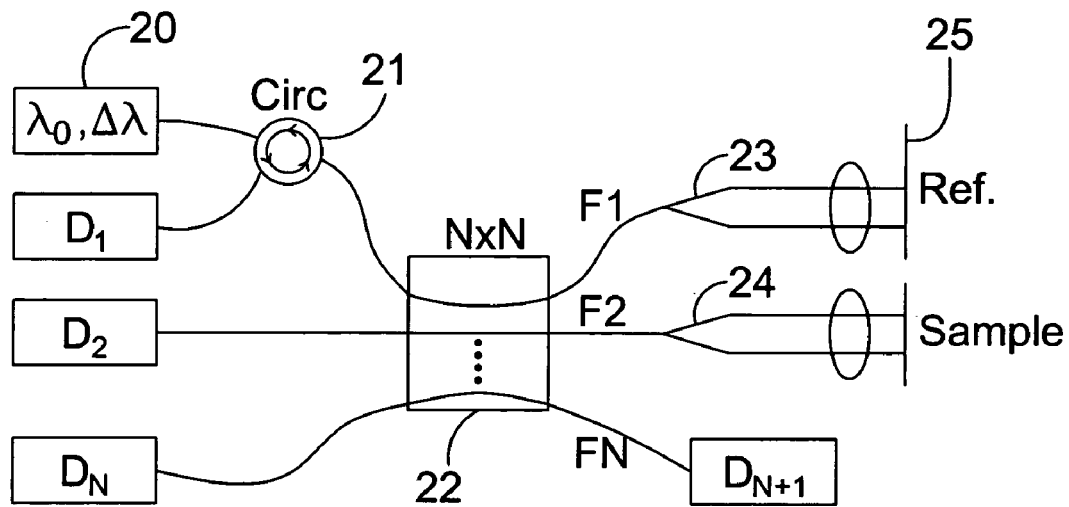
FIG. 8 is a diagram of an N×N coupler-based interferometer generalized to an arbitrarily high order N×N coupler in accordance with one embodiment of the present invention.

FIG. 8 shows an exemplary embodiment of a generalized N×N interferometer formed in accordance with the present invention. This interferometer includes a source 20 which is preferably a broadband source, an optical circulator 21, and an N×N coupler 22 having two outputs for inputting optical signals into reference and sample arms 23 and 24 along respective fibers F1 and F2. The sample arm terminates with a reflector 25. Detectors $D_1-D_{N+1}$ are connected to receive optical beams passing through the coupler. In this embodiment, $N \geq 3$.

While 3×3 coupler-based interferometers are attractive due to their simplicity and efficiency with source light, and suitably designed 3×3 and 4×4 coupler-based interferometers provide direct access to 90°-separated quadrature components of the interferometric signal, higher-order N×N interferometers may be useful in situations where more sophisticated phase extraction schemes than that described in Eq. (3) require denser sampling of the complex plane, or where increased sample reflection utilization efficiency is required in the absence of a circulator in the source arm.

Heterodyne Time-Domain Optical Coherence Tomography

An important potential application of N×N instantaneous quadrature interferometry in heterodyne OCT systems is in Doppler OCT. In Doppler OCT, the sign and magnitude of Doppler shifts arising from moving scatterers within a sample may be recovered from time-frequency analysis of the interferometric signal. This analysis has taken the form of windowed Fourier transform, wavelet transform, or Hilbert transform analysis of interferometric data, either digitized directly or electronically down-mixed using synchronous detection. All of these approaches are non-instantaneous, and involve considerable electronic and/or computational complexity.

Polarization encoding has been used to encode the real and imaginary parts of the complex interferometric signal for Doppler processing. However, the polarization encoding apparatus was complex and expensive and is subject to polarization fading. The use of N×N interferometry for instantaneous recovery of the sign and magnitude of Doppler shifts in Doppler OCT, as described above with reference to FIG. 6, greatly simplifies Doppler OCT.

Homodyne Time-Domain Optical Coherence Tomography

Use of N×N coupler-based low coherence interferometer systems of the present invention allow for near instantaneous extraction of interference phase and amplitude. One major advantage of such an approach is that it eliminates the need to generate a heterodyne beat frequency through which the phase and amplitude information are measured. The technical disadvantages of a heterodyne based system are varied, and some major ones are now discussed.

The time window for extracting time varying amplitude and phase information is limited by the period of the heterodyne beat. In other words, if the sample reflectance where to change in phase shift or amplitude, the quickest the change can be resolved will be in a time window that is at least larger than the heterodyne beat period.

However, N×N homodyne based systems can, in principle, render instantaneous phase and amplitude measurements. In such a situation, the resolving time window and the sensitivity of the measurements trade off with each other. An arbitrarily small time window is achievable with a correspondingly arbitrarily low sensitivity. There is no longer a hard limit on the resolving time window as with the heterodyne situation.

Heterodyne based phase detection is very prone to heterodyne beat frequency fluctuations and finite data sampling rate. In an ideal world, where the heterodyne signal can be sampled with infinite sampling frequency, any beat frequency fluctuations can be detected and corrected for prior to amplitude and phase extraction. Realistically, this is likely not possible and beat frequency fluctuations that are not corrected for will lead to amplitude and phase errors.

Figure 9:
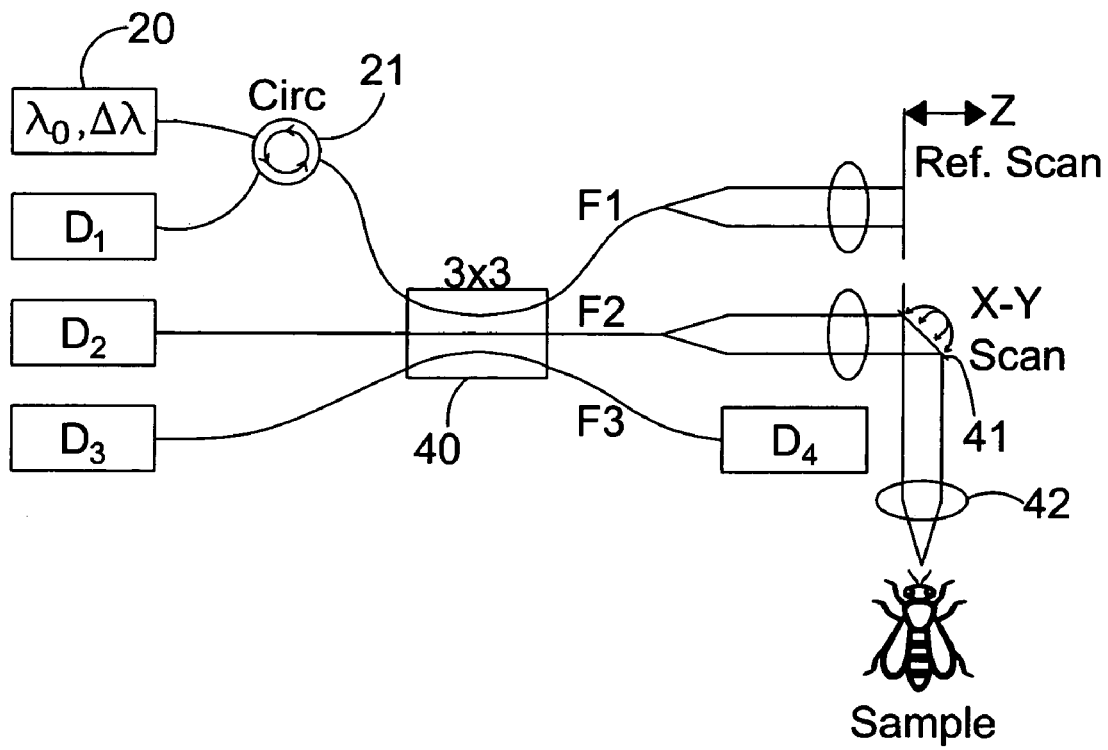
FIG. 9 is a diagram of an N×N coupler-based homodyne low coherence interferometer in accordance with one embodiment of the present invention.

FIG. 9 shows an N×N homodyne-based system in accordance with the present invention which overcomes this problem in two ways. First, it does not require a moving element, which is the most commonly used means for generating the heterodyne frequency. As the non-uniformity of the velocity of the moving element is a major contributor to the heterodyne beat frequency fluctuations, a homodyne-based system is automatically free of this source of error. Second, even if a moving element is present in the interferometer, such as for the purpose of making depth scanning, scan velocity fluctuations can be detected and corrected for by setting the resolving time window at a time scale that is shorter than the fluctuation time scale. (The FIG. 9 embodiment may have a structure similar to the FIG. 8 embodiment except that the N×N couplet is replaced by a 3×3 coupler 40, an X-Y scanning mirror 41 and lens 42 are included along the sample signal path, a Z-scan is performed along the reference signal path, and four detectors $D_1-D_4$ are included).

Heterodyne-based OCT systems generally acquire depth resolved scans (A-scans), since the general incorporation of a moving element to induce the necessary heterodyne beat generally generate a varying optical delay. This optical delay can be used to render depth resolved scans. Heterodyne-based systems can disentangle depth scans from the heterodyne beat generation process through the use of other optical elements, such as an acousto-optic modulator or electro-optic modulator. Such distanglement allows for easier en-face scan pattern (to create en-face images), by then scanning the focal point created by the OCT horizontally within the sample.

However, such systems generally set a limit on the speed of en-face scanning. Each pixel dwell time must be larger than the heterodyne frequency, which leads to slow scan speed due to low heterodyne beat frequency, or high scan speed with a high heterodyne beat frequency. The first situation is not ideal in terms of image acquisition speed. The second requires fast data collection and processing and entails sophisticated instrumentation.

However, an N×N homodyne-based system does not suffer from such limitations. The point of interest can be as easily scanned in depth as it can be scanned laterally. A shorter pixel acquisition time may be traded off by permitting lower sensitivity. The ease of performing en-face scanning means that a homodyne-based en-face scanning optical coherence microscope is possible that exhibits an image acquisition rate that is unobtainable using a heterodyne-based system.

Fourier-Domain Optical Coherence Tomography with Array Detection

An alternate method of coherence gating that does not employ a scanning delay line has been called various terms including spectral radar, Fourier domain OCT (FD-OCT), and complex spectral OCT. In FD-OCT, the positions of reflectors in the sample arm of a Michelson interferometer are resolved by acquiring the optical spectrum of sample light interfered with light from a single, stationary (or phase modulated) reference reflector. The power incident on the array of detectors is related to:

$$P_D(k) = \langle |E_D(k)|^2 \rangle = S(k)R_R + S(k)R_s + 2S(k)\sqrt{R_R R_S}\cos(2k\Delta x) \quad (5)$$

where $S(k)$ is the source spectral shape, $E_D(k)$ is the total field incident on the spectrometer, $R_S$ and $R_R$ are, respectively, the sample and reference reflectivities, and $P_D(k)$ has units of watts per wave number.

The double-pass position of the sample reflector is encoded in the frequency of cosinusoidal variations of $P_D(k)$, while the sample reflectivity is encoded in the visibility of these variations. The spectrally-indexed detector outputs, therefore, represent the real part of the Fourier-transform of the A-scan. This is consistent with the assertion that electronic photodetectors only give the real part of the interferometric signal.

Because Eq. (5) yields the real part of the Fourier transform, a reflector at $+\Delta x$ cannot be distinguished from a reflector at $-\Delta x$:

$$2S(k)\sqrt{R_R R_S}\cos(2k\Delta x) = 2S(k)\sqrt{R_R R_S}\cos(-2k\Delta x). \quad (6)$$

This ambiguity is called complex conjugate ambiguity, and can be resolved by additionally collecting the imaginary part of the interferometric signal $2S(k)(R_R R_S)^{1/2}\cos(2k\Delta x)$, noting that:

$$2S(k)\sqrt{R_R R_S}\sin(2k\Delta x) \ne 2S(k)\sqrt{R_R R_S}\sin(-2k\Delta x) \quad (7)$$

Since the reference arm is not scanned in FD-OCT, the detector signals do not contain an electronic carrier signal related to the phase of the interferometric signal. This constitutes a homodyne detection system and, as such, electronic synchronous detection methods cannot be used to extract the interferometric magnitude and phase.

Phase-shifting interferometry has been utilized to dither the phase of the reference electric field, in order to collect real and imaginary parts on sequential scans. Phase shifting, however, requires a stable and carefully calibrated reference arm step, is not instantaneous, and is sensitive to interferometer drift between phase-shifted acquisitions.

Figure 10:
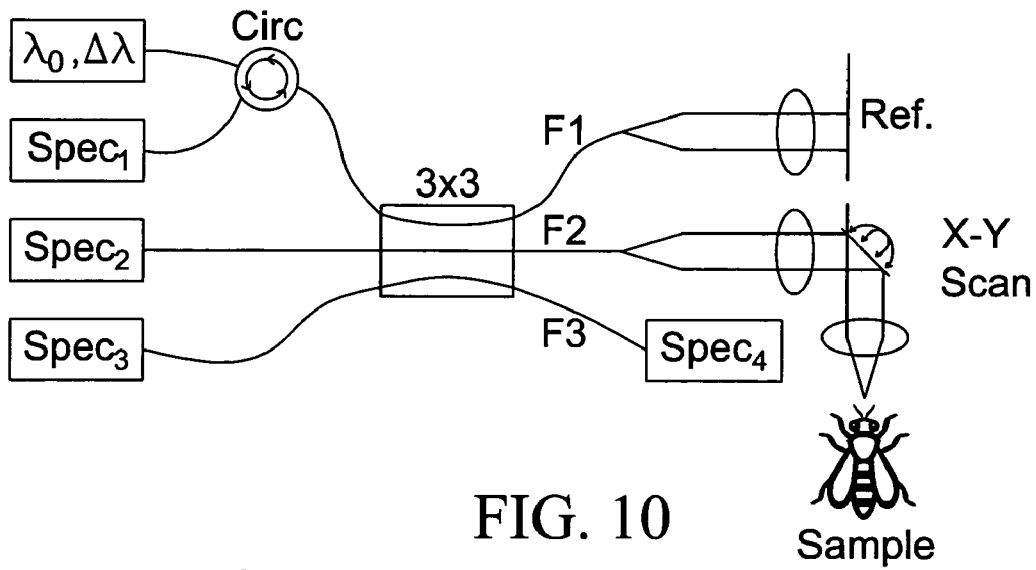
FIG. 10 is a schematic diagram of a Fourier-domain OCT system employing a 3×3 fiber coupler in accordance with one embodiment of the present invention.

FIG. 10 shows an FD-OCT system in accordance with the present invention that uses the techniques described above to acquire a complex interferometric signal, and which removes DC and autocorrelation terms for each spectrometer detector element. This embodiment has a structure similar to FIG. 9, except that detectors $D_1$ through $D_4$ are replaced by the spectrometer detector elements $Spec_1$ through $Spec_4$, respectively, and the reference signal is not subject to a Z-scan. Also, in this embodiment, it must be realized that since array detectors contain a finite number of elements that collect photoelectrons in proportion to incident power and integration time, Eq. (5) must be represented in a discrete form.

If an array contains M elements and interrogates an optical bandwidth of $\Delta k$, the optical channel spacing is $\delta k = \Delta k/M$. The signal thus has values at M evenly spaced wavenumbers $K = \{k_1, k_2, \ldots, k_M\}$. We can write $N_{en}[k_m]$, the number of electrons collected from the $\mu^{th}$ wavenumber on the $n^{th}$ spectrometer as:

$$N_{en}[k_\mu] = \frac{1}{2}\Delta t \delta k S(k)\left[\eta \frac{2\pi}{hck_\mu}\right]\left[R_R + R_S + A + S + 2\sqrt{R_R R_S}\cos(2k_\mu \Delta x + \phi_n)\right], \quad (8)$$

where A is an autocorrelation signal, S is source noise, $\Delta t$ is the detector integration time, $\eta$ is the detector quantum efficiency, h is Planck's constant, and c is the vacuum speed of light. It should be noted that since dispersive spectrometers operate in wavelength and not wavenumber, Eq. (8) is experimentally obtained by numerically resampling the spectrometer data.

As discussed above, the use of detectors (in this case, spectrometers) 1 through 3 allows for the removal of DC terms (i.e. those associated with $R_R$ and $R_S$), autocorrelation terms, and source noise, while the use of detectors 2–4 allows for the removal of DC terms and source noise only. In either case, if $R_s \gg R_R$, autocorrelation terms are small compared to the other terms in Eq. (8), so it is reasonable to assume that $A \sim 0$ if detectors 2–4 are used.

If $N_{en}^{int}[k]$ is defined as the interferometric portion of Eq. (8), then any $N_{en}^{int}[k]$ can be defined as $N_e^{re}[k]$, the real part of the complex interferometric signal. Referring to Eq. (3), and noting that $n, m \in \{1, 2, 3\}$, the imaginary part of the complex interferometric signal is:

$$N_e^{im}[k] = \frac{N_{en}^{int}[k]\cos(\phi_m - \phi_n) - \beta N_{em}^{int}[k]}{\sin(\phi_m - \phi_n)}, \quad (9)$$

$$\beta = \sqrt{\frac{\alpha_{11}\alpha_{1n}\alpha_{12}\alpha_{2n}}{\alpha_{11}\alpha_{1m}\alpha_{12}\alpha_{2m}}}.$$

The aim of FD-OCT is to obtain a depth-reflectivity profile of the sample arm. This can be obtained with the discrete Fourier transform:

$$N_e[x_\delta] = \sum_{\mu=1}^{M}(N_e^{re}[k_\mu] + jN_e^{im}[k_\mu])\text{Exp}[-i2k_\mu x_\delta]. \quad (10)$$

Optical Coherence Tomography with Optical Frequency Domain Reflectometry (Swept-Source OCT)

Figure 11:
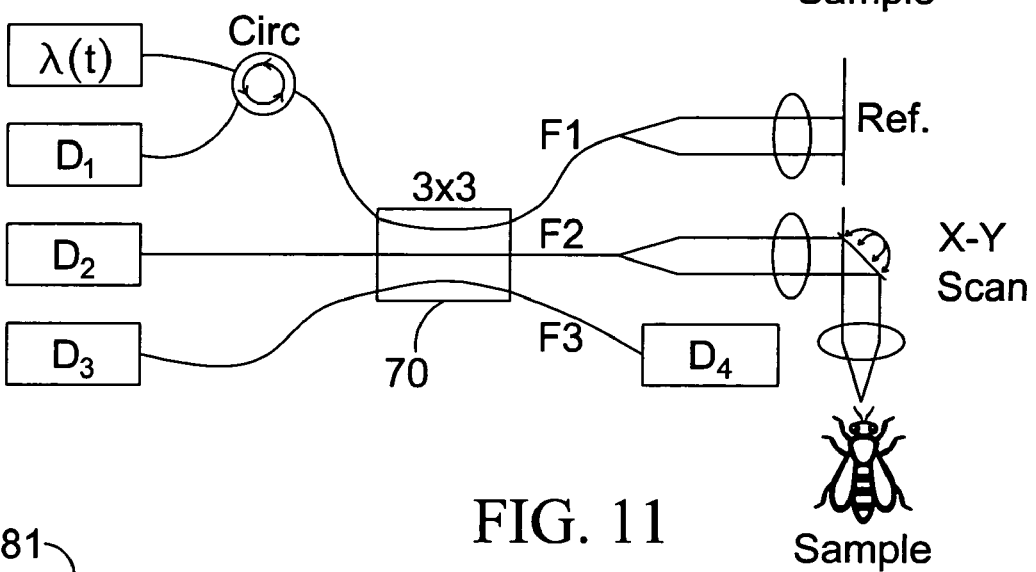
FIG. 11 is a schematic diagram of an OCT system that employs the spectral-domain technique of swept source OCT for depth ranging in accordance with one embodiment of the present invention.

In optical frequency domain reflectometry, the A-scan Fourier transform is acquired by sweeping a narrow-linewidth source over a broad spectral range. FIG. 11 shows an OCT embodiment that employs the frequency-domain technique of optical frequency domain reflectometry for depth ranging, in accordance with one embodiment of the present invention. Use of 3×3 (or more generally an N×N, N>2) coupler 70 allows for acquisition of the entire complex interferometric signal. λ(t) is either a narrow-linewidth source whose wavelength is tuned over time, or a broadband light source filtered by a narrowband optical filter whose passband is tuned over time. Embodiments which use only detectors $D_2$ and $D_3$, $D_1$–$D_3$, or $D_2$–$D_4$ are also possible, with reduced immunity to source fluctuations or autocorrelation terms.

If source sweeping begins at t=0 and ends at Δt, then the detector output is proportional to $P_D(k=Vt+k_{min})$ (Eq. 5). Here, $k_{min}$ is the smallest wavenumber emitted by the source, V has units of wavenumber per second, and V is such that V Δt=$k_{max}$–$k_{min}$=Δk. A-scans are obtained by Fourier transforming the time (and therefore wavenumber) indexed detector output. Since the reference arm is not scanned in OFDR, the detector signals do not contain an electronic carrier signal related to the phase of the interferometric signal. This constitutes a homodyne detection system and, as such, electronic synchronous detection methods cannot be used to extract the interferometric magnitude and phase.

As with FD-OCT, a complex conjugate ambiguity is present if the entire complex interferometric signal is not collected (see Eq. (6), $k=Vt+k_{min}$). The complex signal needs to be extracted with an optical technique (e.g., polarization diversity, phase shifting). DC and autocorrelation terms can be removed with the techniques described above. Unlike FD-OCT, however, it also is possible to remove the DC components by AC coupling the photodetectors. Defining $i_n(k)$ as the interferometric portion of $I_n(k)$ (see Eq. (1), $k=Vt+k_{min}$), and assigning any $i_n(k)$ as the real part of the complex signal (denoted $i_{Re}(k)$ below), then the imaginary part $i_{Im}(k)=2E(\Delta x)(\alpha_{11}\alpha_{1n}\alpha_{12}\alpha_{2n})^{1/2}\sin(2k\Delta x+\phi_n)$, may be obtained by using the cosine sum rule, as (see Eq. (3)):

$$i_{Im}(k) = \frac{i_n(k)\cos(\phi_m - \phi_n) - \beta i_m(k)}{\sin(\phi_m - \phi_n)}, \quad (11)$$

$$\beta = \sqrt{\frac{\alpha_{11}\alpha_{1n}\alpha_{12}\alpha_{2n}}{\alpha_{11}\alpha_{1m}\alpha_{12}\alpha_{2m}}}.$$

The complete complex interferometric signal is $i_{Re}+ji_{Im}$, and the Fourier transform of $i_{Re}+ji_{Im}$ yields the depth-resolved A-scan:

$$ASCAN(x) = \int (i_{Re}+j\times i_{Im})\exp(-jkx)dk \quad (12)$$

Homodyne Phase-Resolved Interferometry

A significant advantage of the N×N coupler-based interferometer systems of the present invention are their ability to measure phase within an arbitrarily small time window. However, phase measured through such means will simply be equal to the optical path difference between the reference and sample interferometer arms. Any vibrational jitters will still be encoded onto the phase as errors.

Fortunately, N×N coupler-based homodyne phase measurement can readily be adapted for use with the numerous interferometer phase measurement techniques that have been developed to circumvent the jitter induced error.

Phase Noise Considerations

Assuming negligible 1/f noise, one can arrive at an order of magnitude estimation of the phase noise as obtained by the heterodyne approach. The shot noise of each measurement is given approximately by sqrt($\epsilon I_o\tau/e$) (numerical scaling factor due to coupling coefficients is presently ignored). The homodyne interference amplitude is equal to 2sqrt($RI_o^2$)$\tau/e$ (numerical scaling factor due to coupling coefficients is presently ignored). The maximum phase error that can be created is when the shot noise and homodyne interference are orthogonal:

$$\theta_{error} = \tan^{-1}(\text{sqrt}(\epsilon I_o\tau/e)/(2\text{sqrt}(RI_o^2)\tau/e)) \approx (½)\text{sqrt}(e/(\epsilon I_o\tau)), \quad (13)$$

where, $\epsilon$ is the detector responsivity, $I_o$ is the light power, $\tau$ is the acquisition time, e is the electron charge, and R is the reflectivity of the sample.

When accounting for coupling coefficients, this error will be corrected slightly. From the error analysis, we can see that higher intensity or longer acquisition time will improve phase sensitivity.

Birefringence OCT

In birefringence OCT, two low coherence light components compose a pair of orthogonal light polarization states. OCT signals are simultaneously acquired for both polarization states and their relative phases can then be processed to determine the depth resolved refractive index difference for the two polarization states within the target sample. Common path interferometer jitters affects both phases equally and, thus, are cancelled out during birefringence computations.

This OCT technique can be implemented in the homodyne mode by simply inputting the two orthogonal polarization states into the OCT system and measuring the homodyne signal at the two polarization states separately. One of the key advantages of operating in homodyne mode is that it is very easy to acquire en-face images.

Wollaston Prism Based Phase Contrast OCT

In this form of phase contrast OCT, low coherence light of a pair of orthogonal polarization states is physically displaced (but propagating in the same direction) prior to incidence on the sample. OCT signals are simultaneously acquired for both polarization states and their relative phases can then be processed to determine the refractive index or height variation between the two focal points.

This OCT technique can be implemented in the homodyne mode by simply inputting the two orthogonal polarization states into the OCT system and measuring the homodyne signal at the two polarization states separately. One of the key advantages of operating in homodyne mode is that it will be very easy to acquire en-face images.

Phase Dispersion OCT

For phase dispersion OCT, low coherence light of two different wavelengths is used in the OCT system. OCT signals are simultaneously acquired for both wavelengths, and their relative phases can then be processed to determine the wavelength dependent refractive index through the depth of the target.

This OCT technique can be implemented in the N×N coupler-based homodyne mode by simply inputting the two wavelengths into the OCT system and measuring the homodyne phases for the two wavelengths.

One of the key advantages of operating in N×N coupler-based homodyne mode is that it will be very easy to acquire en-face images. In addition, the 2 pi ambiguity problem can be substantially mitigated by measuring phase variation with very high spatial resolution. In such a situation, it is possible to depart from the condition that the two wavelengths be harmonically matched, and yet still achieve superior 2 pi ambiguity free measurements.

Phase Referenced Low Coherence Interferometry

For phase referenced low coherence interferometry, low coherence light of one wavelength (or 1 polarization) and monochromatic light of a second wavelength (or the orthogonal polarization) is used in the OCT system. An OCT signal and a monochromatic interference signal are simultaneously acquired for both wavelengths, and their relative phases can then be processed to determine optical path length changes within the sample.

This OCT technique can be implemented in the N×N coupler-based homodyne mode by simply inputting the two wavelengths into the OCT system and measuring the homodyne phases for the two wavelengths.

One of the key advantages of operating in homodyne mode is that it will be very easy to acquire en-face images. In addition, the 2 pi ambiguity problem can be substantially mitigated by measuring phase variation with very high spatial resolution. In such a situation, it is possible to depart from the condition that the two wavelengths be harmonically matched, and yet still achieve superior 2 pi ambiguity free measurements.

This technique, which can be used to measure very small and slow motions in the target (manifested as optical path length changes), has previously been limited in sensitivity and time resolution by the first two problems described in the Homodyne Time-Domain Optical Coherence Tomography section above. With the use of homodyne based approaches, one no longer needs a heterodyne beat generator, and the monitoring of optical path length changes can be made with an arbitrarily small time window.

Magnitude and Phase Resolved Dynamic Light Scattering

Dynamic light scattering (DLS) techniques characterize the time-variations in the properties of light scattered from an illuminated sample. An important class of DLS techniques involves the interferometric mixing of the backscattered sample light with unscattered sample light. The light source used in these techniques can be either CW laser light or broadband light.

One advantage of using broadband light is that it allows for depth-localization within an inhomogenous sample. In either case, the detector measures the real part of the interferometric signal. This is somewhat problematic because the magnitude and phase variations in the interferometric signal are due to different physical processes. For example, the magnitude of the signal is influenced by the total number of particles within the illuminated volume, while phase (speckle) variations are due to subwavelength motions of particles within the illuminated volume. Unfortunately, it is impossible to tell phase from magnitude variations from the real signal alone (see FIG. 7 and associated discussion above).

Figure 12:
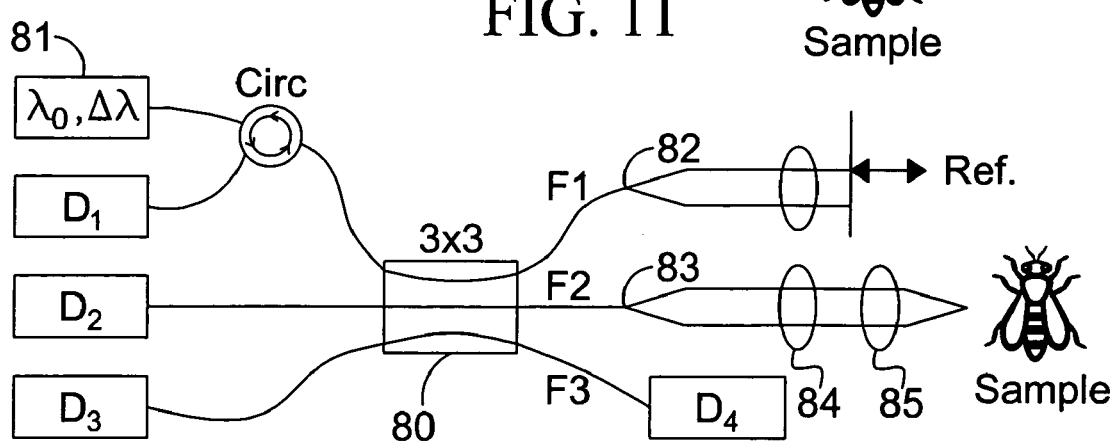
FIG. 12 is a schematic diagram of a homodyne DLS system that employs a 3×3 (or N×N, N>2) fiber coupler in accordance with one embodiment of the present invention.

FIG. 12 shows a homodyne DLS system that employs a 3×3 (or more generally an N×N; N>2) fiber coupler 80 in accordance with one embodiment of the present invention. This embodiment can be used with one or more sources 81 of any bandwidth (e.g., CW where $\Delta\lambda<<\lambda$, broadband where $\Delta\lambda\sim\lambda$). In the case of a broadband light source, the reference arm 82 is scanned to select a particular depth to interrogate in the sample. If the sample arm light 83 is scanned, it is scanned in an en-face manner, as described above. (Optional lenses 84 and 85 may be used to focus this light). This embodiment is a homodyne detection system, and can extract the complex interferometric signal with the techniques described above.

The foregoing embodiments and advantages are merely exemplary and are not to be construed as limiting the present invention. The present teaching can be readily applied to other types of apparatuses. The description of the present invention is intended to be illustrative, and not to limit the scope of the claims.

For example, although fiber couplers are used as the N×N couplers in the embodiments described above, it should be appreciated that bulk optical analog versions of the N×N fiber couplers could be used while still falling within the scope of the present invention. This would enable the extension of the techniques described above to two-dimensional imaging geometries.

Many alternatives, modifications, and variations will be apparent to those skilled in the art. In the claims, means-plus-function clauses are intended to cover the structures described herein as performing the recited function and not only structural equivalents but also equivalent structures.

We claim:

1. A signal processing method, comprising:
   separating interferometric components from non-interferometric components in each of at least two detector signals of an interferometer having a number of N×N couplers;
   scaling the interferometric components from each detector signal;
   generating real and imaginary parts of a complex interferometric signal from the scaled interferometric components; and
   generating depth-resolved sample information from the real and imaginary parts of the complex interferometric signal.

2. The method of claim 1, wherein the detector signals derive from a broadband light source coupled to the interferometer.

3. The method of claim 1, wherein the interferometric components of the detector signals have a predetermined phase difference.

4. The method of claim 3, wherein the interferometric components have orthogonal phases.

5. The method of claim 1, wherein scaling the interferometric components is performed to reduce optical losses.

6. The method of claim 5, wherein the optical losses correspond to at least one of optical path losses and variations in gain between different ones of the detectors.

7. The method of claim 1, wherein separating the interferometric components includes performing high-pass filtering of signals output from the detectors.

8. The method of claim 1, wherein separating the interferometric components includes extracting AC-coupled signals from signals output from the detectors.

9. The method of claim 8, wherein the AC-coupled signals are extracted by:
removing at least one of DC components, source noise components, and auto-correlation terms from outputs of the detectors prior to re-scaling.

10. The method of claim 1, wherein the imaginary part of the complex interferometric signal is computed based on a method derived from the cosine sum rule.

11. The method of claim 10, wherein the cosine sum rule-derived method is based on the following equation:

$$i_m = \frac{i_n \cos(\phi_m - \phi_n) - \beta i_m}{\sin(\phi_m - \phi_n)}$$

where $i_n$ is the real part of a first detector output, $i_m$ is the real part of a second detector output, $\phi_m - \phi_n$ corresponds to a phase shift between the first and second detector outputs, and $\beta$ is a re-scaling parameter.

12. The method of claim 11, wherein the interferometric components have a predetermined phase angle $\phi_m - \phi_n$ between them.

13. The method of claim 12, wherein the predetermined angle is at least substantially 90°.

14. The method of claim 1, further comprising:
calculating a magnitude and phase from the real and imaginary parts of the complex interferometric signal.

15. The method of claim 14, further comprising:
calculating a Doppler shift value based on a time derivative of the calculated phase.

16. The method of claim 15, wherein the Doppler shift value is calculated based on the following equation:

$$\frac{d\text{phase}}{dt} = f_d = \frac{2v}{\lambda} \cos(\theta),$$

where $\lambda$ is optical wavelength, $v$ is reflector velocity, and $\theta$ is the Doppler angle.

17. The method of claim 17, further comprising: estimating reflector velocity based on $$\frac{d\text{phase}}{dt}.$$

18. The method of claim 1, wherein the number of N×N couplers is one.

19. The method of claim 18, wherein $N \geq 3$.

20. The method of claim 19, wherein the detector signals are at least partially derived from outputs of the N×N coupler.

21. The method of claim 20, wherein the interferometric components output from the N×N coupler are adjusted to have predetermined phases, wherein the complex interferometric signal is derived from the phase-adjusted interferometric components.

22. The method of claim 21, wherein the interferometric components of the N×N coupler are adjusted to have orthogonal phases.

23. The method of claim 1, further comprising:
generating a plurality of complex interferometric signals from scaled interferometric components derived from different pairs of detectors in the interferometer; and
generating an average complex interferometric signal from said plurality of complex interferometric signals.

24. The method of claim 1, wherein the interferometer includes a first coupler connected to a second coupler by an optical fiber, and wherein the detector signals respectively correspond to signals remitted from the inputs of the first and second fiber-optic couplers.

25. The method of claim 23, wherein the first coupler is an N×N coupler and the second coupler is an M×M coupler, where $N \neq M$.

26. The method of claim 23, wherein the first coupler is an N×N coupler and the second coupler is an M×M coupler, where $N=M$.

27. The method of claim 1, wherein the interferometer includes an optical circulator connected to one of the fiber-optic couplers, and wherein the detector signals respectively correspond to outputs of the fiber-optic coupler and optical circulator.

28. The method of claim 1, wherein separating the interferometric components includes: measuring DC levels outputs outputs of the detectors prior to re-scaling; and
subtracting the DC levels from the outputs of the detectors respectively.

29. An analyzer, comprising:
an interferometer including at least one fiber-optic coupler;
a number of detectors that detect light from said at least one coupler; and
a processor which acquires interferometric components from signals output from the detectors, scales the interferometric components, generates real and imaginary parts of a complex interferometric signal from the scaled interferometric components and generates depth-resolved sample information from the real and imaginary parts of the complex interferometric signals.

30. The analyzer of claim 29, wherein the light from said at least one coupler derives from a broadband light source coupled to the interferometer.

31. The analyzer of claim 29, wherein said at least one coupler is an N×N coupler, where $N \geq 2$.

32. The analyzer of claim 31, wherein $N \geq 3$.

33. The analyzer of claim 29, wherein the interferometer includes at least a first N×N coupler and a second M×M coupler, and wherein the detector signals are generated from light output from the first and second couplers respectively.

34. The analyzer of claim 33, wherein $N=M$.

35. The analyzer of claim 34, wherein $N \neq M$.

36. The analyzer of claim 29, wherein, the processor phase shifts the interferometric components of the detector signals to have a predetermined phase difference.

37. The analyzer of claim 36, wherein the interferometric components are shifted to have orthogonal phases.

38. The analyzer of claim 29, wherein the processor scales the interferometric components to reduce optical losses.

39. The analyzer of claim 38, wherein the optical losses correspond to at least one of optical path losses and variations in gain between different ones of the detectors.

40. The analyzer of claim 29, wherein the processor separates the interferometric components of each of the detector signals from non-interferometric components.

41. The analyzer of claim 40, wherein the processor separates the interferometric components by performing high-pass or band-pass filtering of the detector signals.

42. The analyzer of claim 40, wherein the processor separates the interferometric components by extracting AC-coupled signals from the detector signals.

43. The analyzer of claim 42, wherein the processor extracts the AC-coupled signals by removing at least one of DC components, source noise components, and auto-correlation terms from the detector outputs prior to re-scaling.

44. The analyzer of claim 29, wherein the processor computes the imaginary part of the complex interferometric signal based on a cosine sum rule.

45. The analyzer of claim 44, wherein the cosine sum rule is based on the following equation:

$$i_m = \frac{i_n \cos(\phi_m - \phi_n) - \beta i_m}{\sin(\phi_m - \phi_n)}$$

where $i_n$ is the real part of a first detector output, $i_m$ is the real part of a second detector output, $\phi_m - \phi_n$ corresponds to a phase shift between the first and second detector outputs, and $\beta$ is a re-scaling parameter.

46. The analyzer of claim 45, wherein the processor scales the interferometric components by adjusting $\phi_m - \phi_n$ to equal a predetermined angle.

47. The analyzer of claim 46, wherein the predetermined angle is at least substantially 90°.

48. The analyzer of claim 29, wherein the processor calculates a magnitude and phase from real and imaginary parts of the complex interferometric signal.

49. The analyzer of claim 48, wherein the processor calculates a Doppler shift value based on a time derivative of the calculated phase.

50. The analyzer of claim 49, wherein the Doppler shift value is calculated based on the following equation:

$$\frac{d\text{phase}}{dt} = f_d = \frac{2v}{\lambda},$$

where $\lambda$ is optical wavelength, $v$ is reflector velocity, and $\theta$ is the Doppler angle.

51. The analyzer of claim 29, wherein the processor generates a plurality of complex interferometric signals from scaled interferometric components derived from different pairs of the detectors, and generates an average complex interferometric signal from said plurality of complex interferometric signals.

52. A method for performing optical coherence tomography, comprising:
  acquiring interferometric components from signals output from at least one fiber-optic coupler located along an optical signal path of the interferometer;
  scaling the interferometric components;
  generating real and imaginary parts of a complex interferometric signal from the scaled interferometric components; and
  instantaneously recovering Doppler shift information from the complex interferometric signal.

53. The method of claim 52, wherein the recovering step includes:
  recovering, from the complex interferometric signal, a sign and magnitude of a Doppler shift arising from moving scatterers in a sample scanned by light from the interferometer.

54. The method of claim 52, wherein the light from said at least one coupler derives from a broadband light source coupled to the interferometer.

55. The method of claim 52, wherein said at least one coupler is an N×N coupler, where $N \geq 2$.

56. The method of claim 55, wherein $N \geq 3$.

57. The method of claim 52, wherein the interferometer includes at least a first N×N coupler and a second M×M coupler, and wherein the detector signals are generated from light output from the first and second couplers respectively.

58. The method of claim 57, wherein $N \neq M$.

59. The method of claim 52, wherein the generating step includes:
  generating the imaginary part of the complex interferometric signal based on a cosine sum rule.

60. The method of claim 59, wherein the cosine sum rule is based on the following equation:

$$i_m = \frac{i_n \cos(\phi_m - \phi_n) - \beta i_m}{\sin(\phi_m - \phi_n)}$$

where $i_n$ is the real part of a first detector output, $i_m$ is the real part of a second detector output, $\phi_m - \phi_n$ corresponds to a phase shift between the first and second detector outputs, and $\beta$ is a re-scaling parameter.

61. The method of claim 60, wherein the first and second detectors detect light along different optical signal paths of the N×N coupler.

62. The method of claim 60, wherein the processor scales the interferometric components by adjusting $\phi_m - \phi_n$ to equal a predetermined angle.

63. The method of claim 62, wherein the predetermined angle is at least substantially 90°.

64. The method of claim 52, further comprising:
  calculating a magnitude and phase from the real and imaginary parts of the complex interferometric signal.

65. The method of claim 64, wherein the recovering step includes obtaining a Doppler shift value based on a time derivative of the calculated phase.

66. The method of claim 64, wherein the Doppler shift value is calculated based on the following equation:

$$\frac{d\text{phase}}{dt} = f_d = \frac{2v}{\lambda},$$

where $\lambda$ is optical wavelength, $v$ is reflector velocity, and $\theta$ is the Doppler angle.

* * * * *